(12) United States Patent
Yen et al.

(10) Patent No.: US 9,013,706 B2
(45) Date of Patent: Apr. 21, 2015

(54) OPTICAL DETECTING APPARATUS AND OPERATING METHOD THEREOF

(71) Applicant: Crystalvue Medical Corporation, Taoyuan (TW)

(72) Inventors: Meng-Shin Yen, Taipei (TW); William Wang, Taoyuan (TW); Chung-Cheng Chou, Taoyuan County (TW)

(73) Assignee: Crystalvue Medical Corporation, Taoyuan (TW)

( * ) Notice: Subject to any disclaimer, the term of this patent is extended or adjusted under 35 U.S.C. 154(b) by 140 days.

(21) Appl. No.: 13/774,820

(22) Filed: Feb. 22, 2013

(65) Prior Publication Data

US 2013/0222808 A1    Aug. 29, 2013

(30) Foreign Application Priority Data

Feb. 24, 2012   (TW) .............................. 101106376 A

(51) Int. Cl.
| | |
|---|---|
| *G01N 21/55* | (2014.01) |
| *G01B 9/02* | (2006.01) |
| *G01N 3/32* | (2006.01) |
| *G01N 11/16* | (2006.01) |
| *G01N 11/00* | (2006.01) |

(52) U.S. Cl.
CPC .................. *G01N 21/55* (2013.01); *G01N 3/32* (2013.01); *G01N 11/16* (2013.01); *G01N 2011/008* (2013.01); *G01N 2203/0094* (2013.01); *G01N 2203/0641* (2013.01)

(58) Field of Classification Search
CPC .............. G01B 3/32; G01B 3/36; G01B 3/38; G01B 21/45; G01B 21/55; G01B 2203/0094; G01B 2203/0641; G01B 2011/008
USPC .................................. 356/445, 450, 503, 504
See application file for complete search history.

(56) References Cited

U.S. PATENT DOCUMENTS

| | | | | |
|---|---|---|---|---|
| 6,673,014 | B2 * | 1/2004 | Badehi et al. ................. | 600/398 |
| 6,786,098 | B2 * | 9/2004 | Bates ............................. | 73/606 |
| 7,123,363 | B2 * | 10/2006 | Puttappa et al. .............. | 356/450 |
| 7,201,720 | B2 * | 4/2007 | Cuzzani et al. ............... | 600/399 |
| 2010/0033723 | A1 * | 2/2010 | Thundat et al. ............... | 356/432 |
| 2013/0063717 | A1 * | 3/2013 | Kawasaki et al. ............. | 356/72 |

FOREIGN PATENT DOCUMENTS

WO        WO 9321820 A1 * 11/1993

* cited by examiner

*Primary Examiner* — Michael A Lyons
(74) *Attorney, Agent, or Firm* — Muncy, Geissler, Olds & Lowe, P.C.

(57) ABSTRACT

An optical detecting apparatus and an operating method thereof are disclosed. The optical detecting apparatus includes a light path module, an actuating module, and a data processing module. The light path module is used to emit a light source to a substance and receive an optical signal generated by the substance reflecting the light source. The actuating module is used to actuate the substance to generate a vibration. The data processing module is used to record and analyze a detected result related to the material properties of the substance and adjust detecting parameters of the light path module and the actuating module respectively.

5 Claims, 5 Drawing Sheets

OPTICAL DETECTING APPARATUS AND OPERATING METHOD THEREOF

BACKGROUND OF THE INVENTION

1. Field of the Invention

The invention relates to optical detection, and in particular, to an optical detecting apparatus capable of detecting a mechanical property and an optical property of a substance simultaneously through a non-contact and non-destructive method and an operating method thereof.

2. Description of the Prior Art

In general, when we determine a function of a substance, the mechanical property and optical property of the substance will be used as important reference factors, and whether the substance still has the function will be judged by detecting the reference factors.

Common substance property detecting methods usually can be divided into two types: destructive type and non-destructive type. The destructive type substance property detecting method uses external force to destruct original system of the substance to obtain slices or samples of the substance; the non-destructive type substance property detecting method uses non-destructive methods such as light, electricity, magnetic, or sonic to directly detect the substance. For some specific regions, such as detection done to living organisms, the non-destructive type substance property detecting method is preferred to reduce the damage caused to the living organisms.

In various non-destructive type substance property detecting methods, ultrasound detecting method is a mature substance property detecting method and widely used to detect different substances. However, because the resolution of the ultrasound detecting method is not good enough, when the user wants to use ultrasound detecting method to analyze the substance in detail, it is hard to obtain good detected result, especially for detecting the physiological organizational structure system or organism (animal and plant).

Therefore, an optical detecting apparatus and an operating method thereof are disclosed in the invention to solve the above-mentioned problems.

SUMMARY OF THE INVENTION

An embodiment of the invention is an optical detecting apparatus. In this embodiment, the optical detecting apparatus includes a light path module, an actuating module, and a data processing module. The light path module is used to emit a light source to a substance and receive an optical signal generated by the substance reflecting the light source. The actuating module is used to actuate the substance to generate a vibration. The data processing module is used to record and analyze a detected result related to the material properties of the substance and adjust detecting parameters of the light path module and the actuating module respectively.

In practical applications, the detected result includes a mechanical property and an optical property of the substance, the mechanical property of the substance includes an elasticity coefficient and a viscosity coefficient and the optical property of the substance includes a light penetrating property, a light absorbing property, and a light reflecting property. The light path module includes a plurality of optical units having different functions to provide a light interference effect, the plurality of optical units at least includes an emitting unit and a receiving unit, the emitting unit is used for emitting the light source to the substance and the receiving unit is used for receiving the optical signal generated by the substance reflecting the light source.

Another embodiment of the invention is an optical detecting apparatus operating method. In this embodiment, the optical detecting apparatus includes a light path module, an actuating module, and a data processing module, the method includes following steps of (a) the light path module emitting a light source to a substance and receiving an optical signal generated by the substance reflecting the light source; (b) the actuating module actuating the substance to generate a vibration; (c) the data processing module recording and analyzing a detected result related to material properties of the substance and adjusting detecting parameters of the light path module and the actuating module respectively.

Compared with the prior art, the optical detecting apparatus and operating method thereof in the invention use the optical interference technology and actuate the substance to generate vibration, so that the mechanical property and the optical property of the substance can be detected simultaneously through a non-contact and non-destructive method to obtain better substance property detected results. And, the application range of the optical detecting apparatus and operating method thereof in the invention is very wide, not only suitable for living organisms, but also for non-living, and can be further cooperated with a matrix probe and a scanning platform to rapidly finish numerous detections. In addition, the optical detecting apparatus and operating method thereof in the invention can also make different parameter setups toward the known substance and the unknown substance respectively to obtain better confirmation and detected results.

The advantage and spirit of the invention may be understood by the following recitations together with the appended drawings.

BRIEF DESCRIPTION OF THE APPENDED DRAWINGS

DETAILED DESCRIPTION OF THE INVENTION

Figure 1:
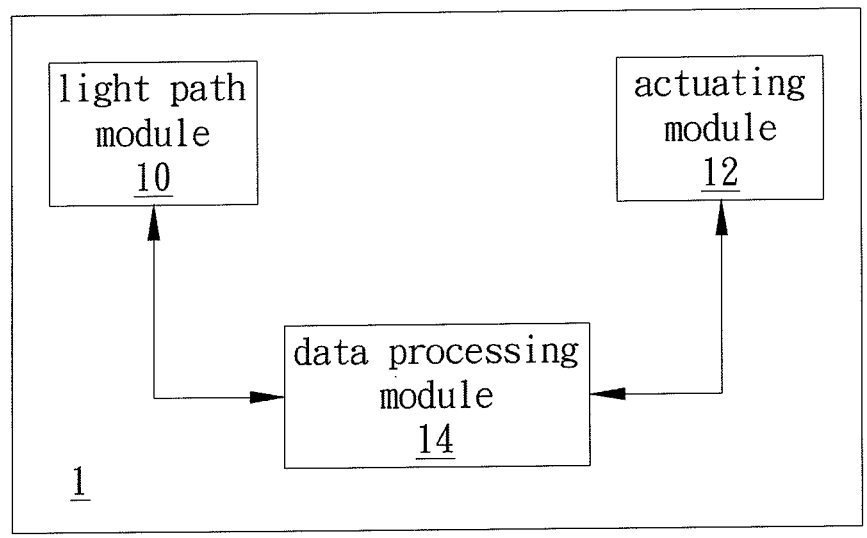
FIG. 1 illustrates a function block diagram of the optical detecting apparatus in a preferred embodiment of the invention.

A preferred embodiment of the invention is an optical detecting apparatus. Please refer to FIG. 1. FIG. 1 illustrates a function block diagram of the optical detecting apparatus in this embodiment. As shown in FIG. 1, the optical detecting apparatus 1 includes a light path module 10, an actuating module 12, and a data processing module 14. Wherein, the data processing module 14 is coupled to the light path module 10 and the actuating module 12 respectively.

Next, the modules of the optical detecting apparatus 1 and their functions will be introduced in detail.

Figure 2:
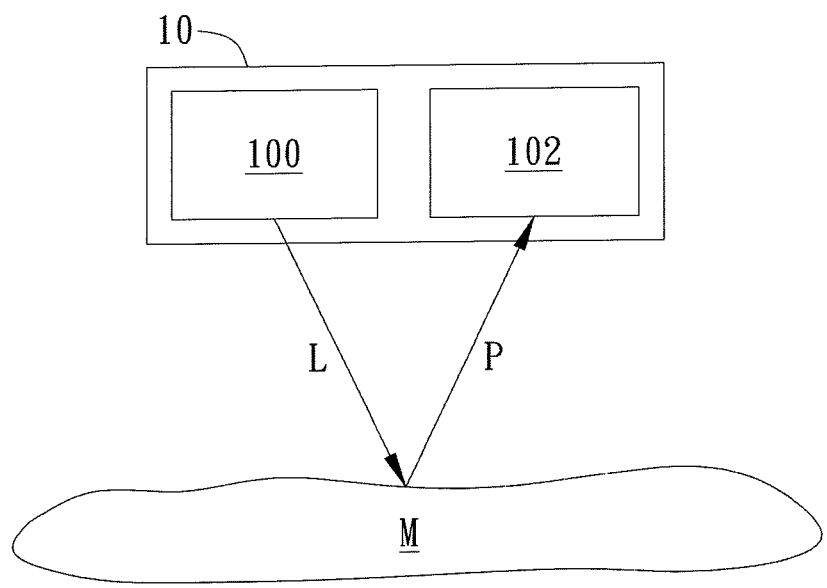
FIG. 2 illustrates an embodiment of the light path module shown in FIG. 1.

In this embodiment, the light path module 10 is used to emit a light source to a substance and receive an optical signal generated by the substance reflecting the light source. In fact, the light path module 10 can include a plurality of optical units having different functions respectively to provide a light interference effect, so that it can perform light interference detection in depth direction to different regions on the substance. Please refer to FIG. 2. FIG. 2 illustrates an embodiment of the light path module 10 shown in FIG. 1.

As shown in FIG. 2, the light path module 10 can include an emitting unit 100 and a receiving unit 102. Wherein, the emitting unit 100 is used for emitting the light source L to the substance M and the receiving unit 102 is used for receiving the optical signal P generated by the substance M reflecting the light source L. It should be noticed that the light path module 10 of the optical detecting apparatus 1 can include other optical units, not limited to the emitting unit 100 and the receiving unit 102 shown in FIG. 2. In fact, the light path module 10 can use the optical coherence tomography (OCT) technology to perform a deep detection on the substance M in depth direction, but not limited to this.

The actuating module 12 is used for actuating the substance M to generate a vibration, so that the substance M can be under a stationary state and a vibration state in different times respectively. In fact, the actuating module 12 can be designed in contact type or non-contact type using a pneumatic method or a sonic method without specific limitations. The data processing module is used for recording and analyzing a detected result related to material properties of the substance M and adjusting detecting parameters of the light path module 10 and the actuating module 12 respectively.

In practical applications, the detected result of the material properties of the substance M can include a mechanical property and an optical property of the substance M. For example, the mechanical property of the substance M can include an elasticity coefficient and a viscosity coefficient, and the optical property of the substance M includes a light penetrating property, a light absorbing property, and a light reflecting property, but not limited to this. The detecting parameters of the light path module 10 can include a light emitting wave length, a light emitting energy, a light emitting angle, and a light receiving angle; the detecting parameters of the actuating module 12 can include an actuating energy, an actuating frequency/wave length, an actuating time, and an actuating strength.

In detail, the data processing module 14 not only records and adjusts actuating parameters used by the actuating module 12 to actuate the substance M to generate the vibration, but also reads different optical signals received by the light path module 10 and calculates a mechanical property and an optical property of the substance M accordingly, and the different optical signals are generated by the substance M reflecting the light source L under the stationary state and the vibration state respectively.

Figure 3:
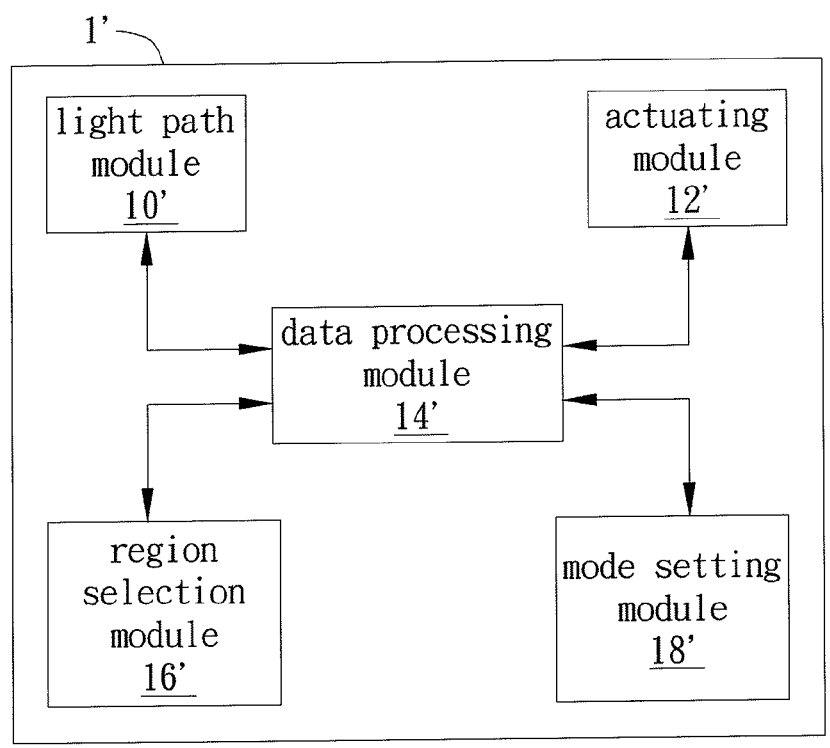
FIG. 3 illustrates a function block diagram of the optical detecting apparatus in another embodiment of the invention.

Then please refer to FIG. 3. FIG. 3 illustrates a function block diagram of the optical detecting apparatus in another embodiment of the invention. As shown in FIG. 3, the optical detecting apparatus 1' not only includes a light path module 10', an actuating module 12', and a data processing module 14', but also includes a region selection module 16', and a mode setting module 18'. Wherein, the data processing module 14' is coupled to the light path module 10', the actuating module 12', the region selection module 16', and the mode setting module 18' respectively.

In this embodiment, the region selection module 16' is used for selecting a region on the substance for the optical detecting apparatus 1' to detect. It should be noticed that during the process of the region selection module 16' selecting the region to be detected, the light path module 10' and the actuating module 12' are started, and the data processing module 14' can still adjust the detecting parameters of the light path module 10' and the actuating module 12' to be better ones.

In fact, because the substance is in continuum state, the user can use the region selection module 16' to select a better region on the substance to be detected, so that the regions not suitable to be detected, such as the polluted region or the vibration node area, will be avoided. In addition, the region selected by the region selection module 16' can be recorded and saved for the following reference.

As stated above, because during the process of the region selection module 16' selecting the region to be detected, the optical properties (ex., penetrating, reflection, and absorption) of the layer structure in depth direction of the substance have preliminary confirmations, when the optical detecting apparatus 1' performs function quality confirmation on the known substance, the data processing module 14' can perform the comparison of the data to judge whether the substance has other structures, or whether the optical properties of the substance is different from the default reference value.

In this embodiment, the mode setting module 18' is used for selectively setting the optical detecting apparatus 1' under a known substance mode or an unknown substance mode to perform different detecting parameter setups for the known substance and the unknown substance.

Under the known substance mode, the data processing module 14' will rapidly compare the detected result of the substance M with a plurality of default detected results stored in a database to confirm whether the substance is a specific known substance. In general, the known substance mode is most applied to confirm the quality of the function of the substance; for example, for performing sample detection on animal and plant agricultural products or human tissues and organs.

Under the unknown substance mode, since the substance is detected first time, the user has to first select a laminar property of the substance, such as overall, single layer, or multiple layers, and then the data processing module 14' will select corresponding calculating mode (ex., rigid body+viscoelastic, single-layer viscoelastic, or complex viscoelastic) and the detecting parameters of the light path module 10' and the actuating module 12' from the database according to the laminar property of the substance for the light path module 10' and the actuating module 12' to detect the substance to obtain better actuating method and detected results.

When the optical detecting apparatus 1' starts to detect, the actuating module 12' will perform several times of vibration start-up driving on the substance, and the light path module 10' will continuously perform optical interference detection on substance under the stationary state and the vibration state. The data processing module 14' will synchronously record the actuating parameters of the actuating module 12' and integrate them with the light detected data obtained by the light path module 10'. Then, the data processing module 14' will cooperate with the known substance mode or the unknown substance mode set by the mode setting module 18' to calculate and analyze the above-mentioned detected data to obtain the detected result including the mechanical property and the optical property of the substance and display the detected result.

In order to fully introduce the practical operation condition of the optical detecting apparatus in the invention, an example of the optical detecting apparatus detecting on the animal substance will be introduced as follows.

Figure 4:
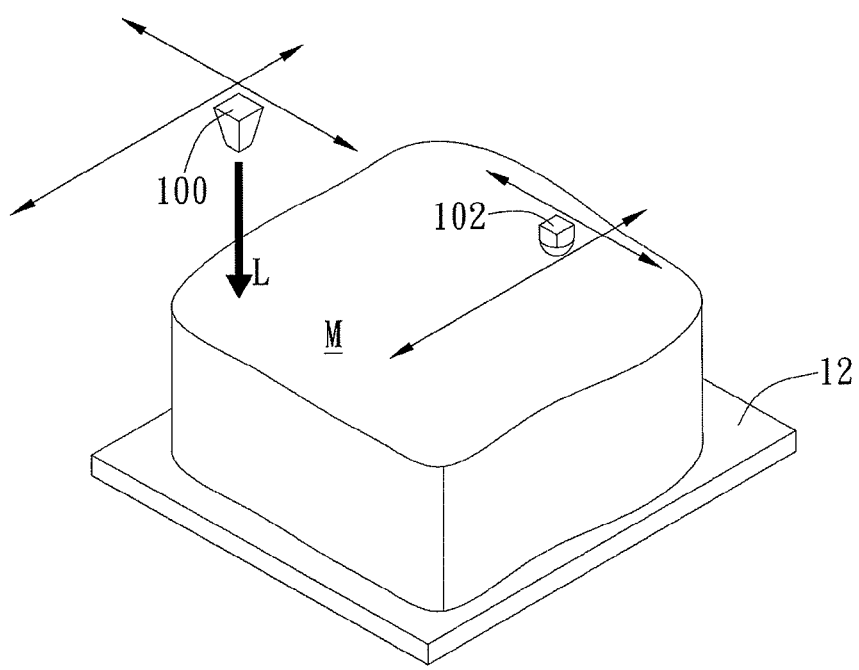
FIG. 4 illustrates a schematic diagram of the optical detecting apparatus detecting on the animal substance.

Please refer to FIG. 4. FIG. 4 illustrates a schematic diagram of the optical detecting apparatus detecting on the animal substance. As shown in FIG. 4, the actuating module 12 actuates the substance M to generate a vibration. It should be noticed that FIG. 4 illustrates the contact type design of the actuating module 12 contacting with the substance M. In fact, the actuating module 12 can also be non-contact type design; for example, using a pneumatic method or a sonic method to actuate the substance M to generate the vibration. It depends on practical needs.

The emitting unit 100 and the receiving unit 102 of the light path module 10 will synchronously perform light interference detection on different regions of the substance M in depth direction. In practical applications, no matter the probe or driver of the light path module 10 or actuating module 12 can be designed in matrix type or cooperated with a scanning platform to detect different regions of the substance M. In addition, the probe or driver of the light path module 10 or actuating module 12 can be designed with the angle rotation function to enhance the accuracy of the detected results.

Figure 5A:
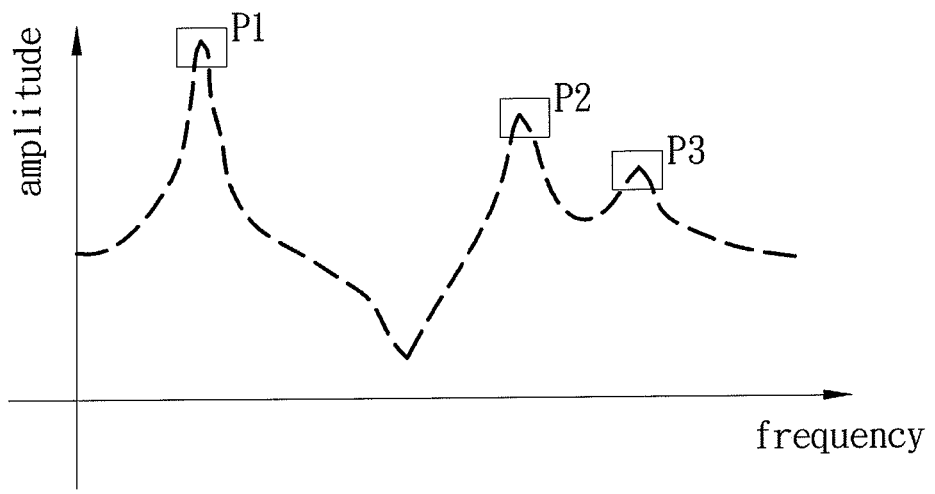
FIG. 5A illustrates that the resonance frequency is obtained from the frequency-domain detection results.
Figure 5B:
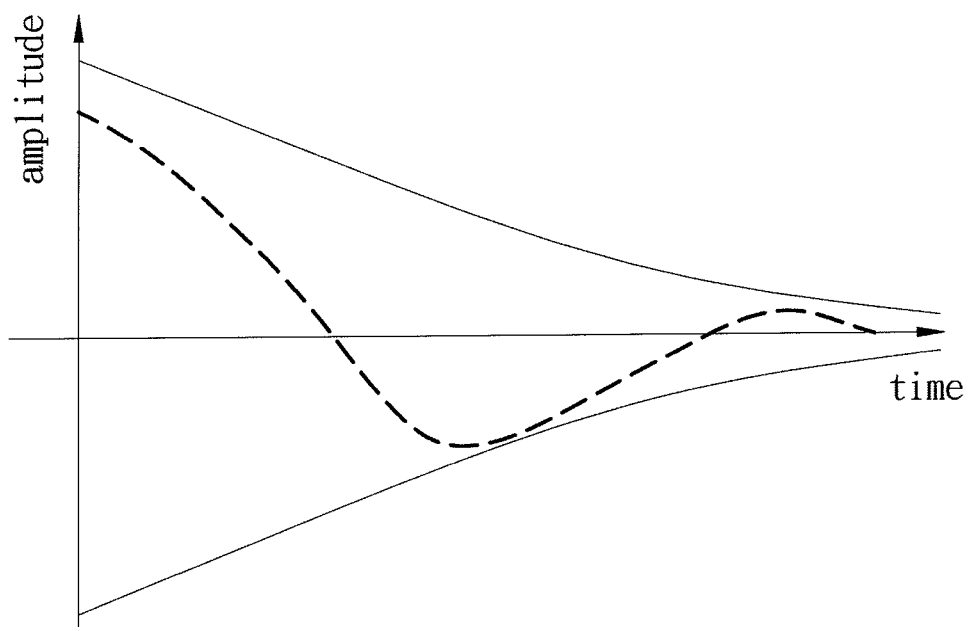
FIG. 5B illustrates that the mechanical property of the substance is obtained from the changes in the amplitude signal of the time-domain.

The dynamic detected result (displacement/deformation amount) obtained from different positions on the substance M can be used to select the region to be detected and to set better actuating parameter of the actuating module 12. Then, after the data comparison is done, it can be confirmed whether the optical property of the substance M in depth direction is the same with the default data, so that one of the default detecting modes can be directly selected to perform practical detection. After the detecting mode is selected, it can connect to substance mechanical property analog model stored in the database, such as system model formed by single or multiple spring and damper, but not limited to this. Therefore, when the detection starts, the selected detecting mode will be used to perform the data operation analysis. For example, a resonance frequency can be first obtained according to the frequency-domain detection operation results (please refer to FIG. 5A, different amplitude peaks P1~P3 can be obtained by changing the driving frequency of the actuating module 12), and then reasonable mechanical property (the elasticity coefficient and viscosity coefficient, please refer to FIG. 5B) of the substance M can be determined according to the time-domain signal amplitude changes (the vibration start-up frequency of the actuating module 12 approaches the resonance frequency). At last, the optical property and the mechanical property of the substance M can be obtained.

Figure 6:
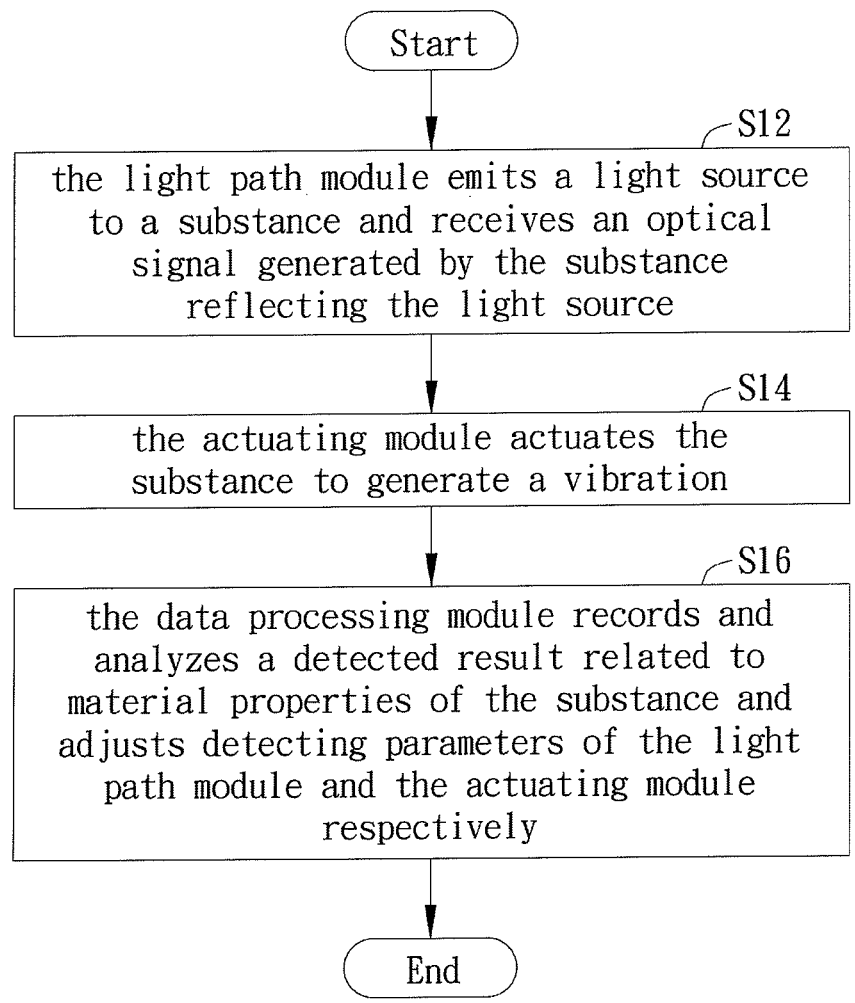
FIG. 6 illustrates a flowchart of the optical detecting apparatus operating method in another embodiment of the invention.

Another embodiment of the invention is an optical detecting apparatus operating method. In this embodiment, the optical detecting apparatus includes a light path module, an actuating module, and a data processing module. Please refer to FIG. 6. FIG. 6 illustrates a flowchart of the optical detecting apparatus operating method in this embodiment.

As shown in FIG. 6, at first, the method performs step S12, the light path module emits a light source to a substance and receives an optical signal generated by the substance reflecting the light source. Then, the method performs step S14, the actuating module actuates the substance to generate a vibration. In fact, the order of performing the steps S12 and S14 can be changed or even the steps S12 and S14 can be performed simultaneously. Afterward, the method performs step S16, the data processing module records and analyzes a detected result related to material properties of the substance and adjusts detecting parameters of the light path module and the actuating module respectively.

Figure 7:
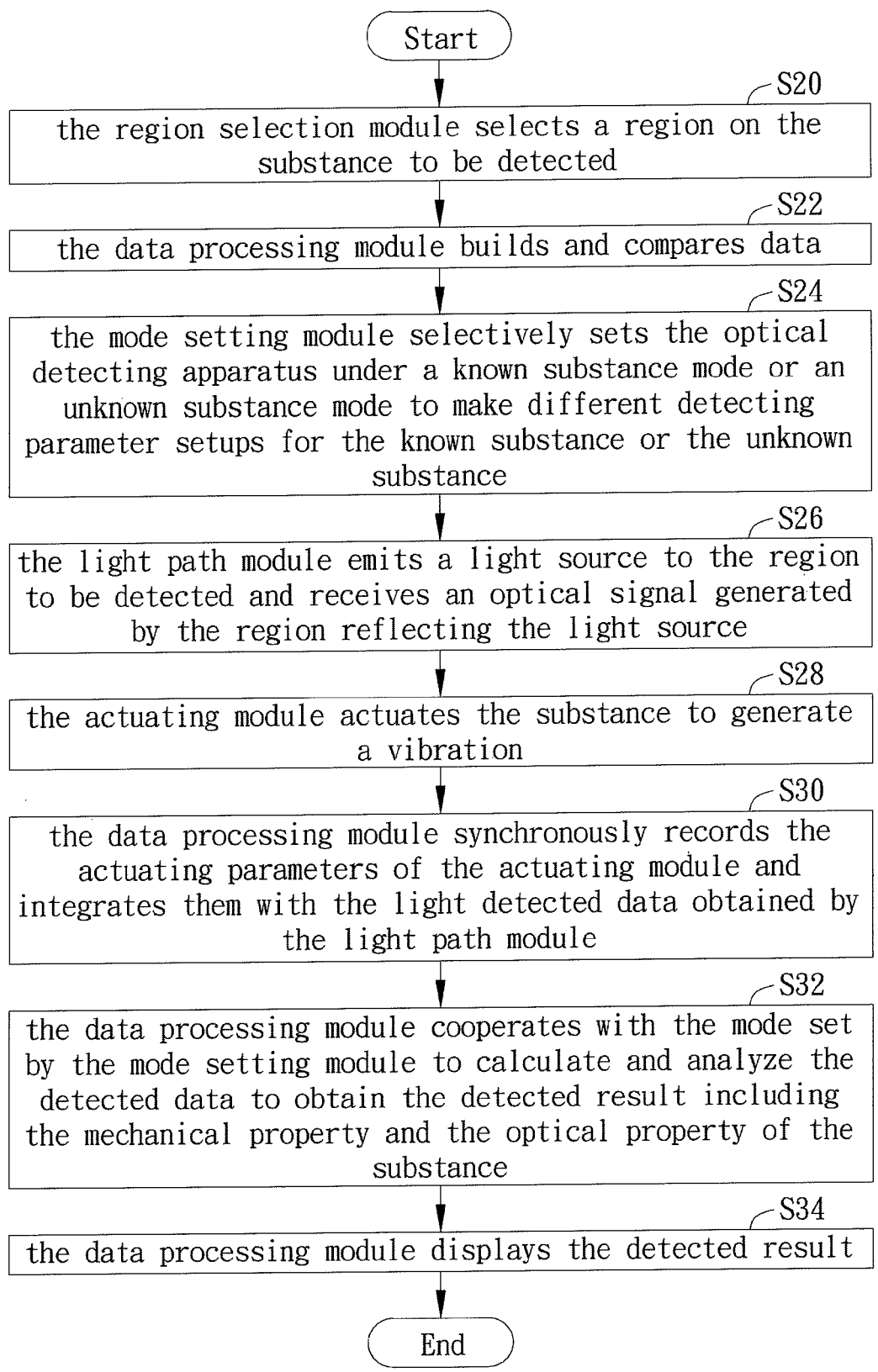
FIG. 7 illustrates a flowchart of the optical detecting apparatus operating method in another embodiment of the invention.

In another embodiment, the optical detecting apparatus not only includes a light path module, an actuating module, and a data processing module, but also includes a region selection module and a mode setting module. Please refer to FIG. 7. The method first performs step S20, the region selection module selects a region on the substance to be detected. Then, in step S22, the data processing module builds and compares data. Then, in step S24, the mode setting module selectively sets the optical detecting apparatus under a known substance mode or an unknown substance mode to make different detecting parameter setups for the known substance or the unknown substance.

Under the known substance mode, the data processing module will rapidly compare the detected result of the substance with a plurality of default detected results stored in a database to confirm that the substance is a specific known substance; under the unknown substance mode, the user first selects a laminar property of the substance, and then the data processing module will select corresponding detecting parameters of the light path module and the actuating module from the database according to the laminar property for the light path module and the actuating module to detect the substance.

Then, the optical detecting apparatus will start to detect. In step S26, the light path module emits a light source to the region to be detected and receives an optical signal generated by the region reflecting the light source. In step S28, the actuating module actuates the substance to generate a vibration. In fact, the order of performing the steps S26 and S28 can be changed or even the steps S26 and S28 can be performed simultaneously. In step S30, the data processing module synchronously records the actuating parameters of the actuating module and integrates them with the light detected data obtained by the light path module. In step S32, the data processing module cooperates with the mode set by the mode setting module to calculate and analyze the detected data to obtain the detected result including the mechanical property and the optical property of the substance. At last, in step S34, the data processing module displays the detected result.

Compared with the prior art, the optical detecting apparatus and operating method thereof in the invention use the optical interference technology and actuate the substance to generate vibration, so that the mechanical property and the optical property of the substance can be detected simultaneously through a non-contact and non-destructive method to obtain better substance property detected results. And, the application range of the optical detecting apparatus and operating method thereof in the invention is very wide, not only suitable for living organisms, but also for non-living, and can be further cooperated with a matrix probe and a scanning platform to rapidly finish numerous detections. In addition, the optical detecting apparatus and operating method thereof in the invention can also make different parameter setups toward the known substance and the unknown substance respectively to obtain better confirmation and detected results.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A method of operating an optical detecting apparatus, comprising following steps of:

(a) emitting a light to a substance and receiving an optical signal generated by the substance reflecting the light;
(b) actuating the substance to generate a vibration; and
(c) recording and analyzing a detected result related to material properties of the substance and adjusting detecting parameters of the optical detecting apparatus respectively, wherein the detected result comprises a mechanical property and an optical property of the substance.

2. The method of claim 1, wherein the mechanical property of the substance comprises an elasticity coefficient and a viscosity coefficient and the optical property of the substance comprises a light penetrating property, a light absorbing property, and a light reflecting property, the detecting parameters of the optical detecting apparatus comprise a light emitting wave length, a light emitting energy, a light emitting angle, a light receiving angle, an actuating energy, an actuating frequency/wave length, an actuating time, and an actuating strength, the optical detecting apparatus is designed in contact type or non-contact type using a pneumatic method or a sonic method.

3. The method of claim 1, wherein the optical detecting apparatus comprises a plurality of optical units having different functions to provide a light interference effect.

4. The method of claim 3, further comprising following steps of:

recording and adjusting an actuating parameter used to actuate the substance to generate the vibration;
the substance reflecting the light under a stationary state and a vibration state respectively to generate different optical signals; and
reading the different optical signals and calculating the mechanical property and the optical property of the substance accordingly.

5. The method of claim 1, further comprising following steps of:

selecting a region on the substance to be detected; and
selectively setting the optical detecting apparatus under a known substance mode or an unknown substance mode;
wherein, under the known substance mode, the optical detecting apparatus will rapidly compare the detected result of the substance with a plurality of default detected results stored in a database to confirm that the substance is a specific known substance; under the unknown substance mode, a user first selects a laminar property of the substance, and then the optical detecting apparatus will select corresponding detecting parameters of the optical detecting apparatus from the database according to the laminar property for the optical detecting apparatus to detect the substance.

* * * * *